US008357805B2

(12) United States Patent
Arad et al.

(10) Patent No.: US 8,357,805 B2
(45) Date of Patent: *Jan. 22, 2013

(54) (1R,1'R)-ATRACURIUM SALTS SEPARATION PROCESS

(75) Inventors: Oded Arad, Rehovot (IL); Elena Ostrovsky, Rishon Le-Zion (IL)

(73) Assignee: CHEMAGIS Ltd., Bnei Brak (IL)

( * ) Notice: Subject to any disclaimer, the term of this patent is extended or adjusted under 35 U.S.C. 154(b) by 460 days.

This patent is subject to a terminal disclaimer.

(21) Appl. No.: 12/601,734

(22) PCT Filed: Mar. 5, 2008

(86) PCT No.: PCT/IL2008/000290
§ 371 (c)(1),
(2), (4) Date: Nov. 24, 2009

(87) PCT Pub. No.: WO2008/155752
PCT Pub. Date: Dec. 24, 2008

(65) Prior Publication Data
US 2010/0174082 A1 Jul. 8, 2010

Related U.S. Application Data

(60) Provisional application No. 60/944,597, filed on Jun. 18, 2007.

(51) Int. Cl.
*A61K 31/4725* (2006.01)
*C07D 401/12* (2006.01)
(52) U.S. Cl. ........................... 546/140; 514/308
(58) Field of Classification Search .................. 514/308; 546/140
See application file for complete search history.

(56) References Cited

U.S. PATENT DOCUMENTS

| | | | |
|---|---|---|---|
| 4,179,507 A | 12/1979 | Stenlake et al. |
| 4,491,665 A | 1/1985 | El-Sayad et al. |
| 4,701,460 A | 10/1987 | El-Sayad et al. |
| 4,761,418 A | 8/1988 | Swaringen, Jr. et al. |
| 4,851,537 A | 7/1989 | Noyori et al. |
| 4,988,815 A | 1/1991 | Andre et al. |
| 5,240,939 A | 8/1993 | Demko |
| 5,453,510 A | 9/1995 | Hill et al. |
| 5,556,978 A | 9/1996 | Hill et al. |
| 5,684,154 A | 11/1997 | Chamberlin et al. |
| 6,015,903 A | 1/2000 | Viergutz et al. |
| 6,177,445 B1 | 1/2001 | Bigham et al. |
| 6,187,789 B1 | 2/2001 | Bigham et al. |
| 6,830,933 B2 | 12/2004 | Lemmens et al. |
| 7,265,099 B1 | 9/2007 | Bom et al. |
| 2006/0009485 A1 | 1/2006 | Friedman et al. |
| 2008/0139482 A1 | 6/2008 | Savarese |
| 2009/0156562 A1 | 6/2009 | Winch |
| 2010/0016596 A1 | 1/2010 | Pozzoli et al. |
| 2010/0087650 A1 | 4/2010 | Ostrovsky et al. |
| 2010/0099878 A1 | 4/2010 | Arad et al. |
| 2010/0168431 A1 | 7/2010 | Naddaka et al. |
| 2010/0184988 A1 | 7/2010 | Naddaka et al. |
| 2010/0234602 A1 | 9/2010 | Arad et al. |
| 2010/0256381 A1 | 10/2010 | Arad et al. |
| 2010/0298570 A1 | 11/2010 | Segnalini et al. |
| 2011/0185796 A1 | 8/2011 | Arad et al. |

FOREIGN PATENT DOCUMENTS

| | | |
|---|---|---|
| CN | 101084896 A | 12/2007 |
| CN | 101337935 A | 1/2009 |
| CN | 101337936 A | 1/2009 |
| CN | 101475530 A | 7/2009 |
| CN | 101845017 A | 9/2010 |
| EP | 0 219 616 | 4/1987 |
| EP | 0219616 | 4/1987 |
| WO | WO 92/00965 A1 | 1/1992 |
| WO | WO 9200965 A1 * | 1/1992 |
| WO | WO 98/42675 A1 | 10/1998 |
| WO | WO 2007/091753 A1 | 8/2007 |
| WO | WO 2008/107887 A2 | 9/2008 |
| WO | WO 2008/117271 A1 | 10/2008 |
| WO | WO 2008/132746 A1 | 11/2008 |
| WO | WO 2008/132748 A1 | 11/2008 |
| WO | WO 2009/007946 A1 | 1/2009 |
| WO | WO 2009/057086 A1 | 5/2009 |
| WO | WO 2009/106547 A1 | 9/2009 |
| WO | WO 2009/133556 A2 | 11/2009 |
| WO | WO 2010/128518 A2 | 11/2010 |
| WO | WO 2010/128519 A1 | 11/2010 |

OTHER PUBLICATIONS

ICH Guideline, International Conference on Harmonization of Technical Requirements of Registration of Pharmaceuticals for Human Use (ICH), ICH Q3CR4 residual solvents MEDIA5254 (Feb. 2009).
European Patent Office, International Search Report in International Patent Application No. PCT/IL2008/000291 (Jul. 4, 2008).
European Patent Office, International Search Report in International Patent Application No. PCT/IL2008/000290 (Jul. 7, 2008).
European Patent Office, International Search Report in International Patent Application No. PCT/IL2008/000289 (Sep. 5, 2008).
European Patent Office, International Search Report in International Patent Application No. PCT/IL2008/000586 (Aug. 27, 2008).
European Patent Office, International Search Report in International Patent Application No. PCT/IL2008/000589 (Aug. 21, 2008).
European Patent Office, International Search Report in International Patent Application No. PCT/IL2008/000590 (Aug. 29, 2008).
European Patent Office, International Search Report in International Patent Application No. PCT/IL2008/001329 (Feb. 4, 2009).
U.S. Patent & Trademark Office, International Search Report in International Patent Application No. PCT/IL2009/000452 (Aug. 12, 2009).
Lindon et al. "Directly coupled HPLC-NMR and HPLC-NMR-MS in pharmaceutical research and development," Journal of Chromatography B : Biomedical Applications, Elsevier Science Publishers, NL, vol. 748, No. 1, pp. 233-258 (Oct. 1, 2000).
Liu et al. "High-performance liquid chromatography of atracurium besylate," Yao Hsueh Hsueh Pao—Acta Pharmaceutica Sinica, Beijing, CN, vol. 29, No. 1, pp. 68-73 (Jan. 1, 1994).

(Continued)

*Primary Examiner* — Joseph Kosack
*Assistant Examiner* — Matthew Coughlin
(74) *Attorney, Agent, or Firm* — Leydig, Voit & Mayer, Ltd.

(57) ABSTRACT

The present invention provides an improved method for obtaining cisatracurium besylate, which preferably chromatographically separating cisatracurium besylate from a mixture of (1R,1'R)-atracurium isomers via flash chromatography.

12 Claims, No Drawings

OTHER PUBLICATIONS

Mistry et al. "Directly Coupled Chiral HPLC-NMR and HPLC-CD Spectroscopy as Complementary Methods for Structural and Enantiomeric Isomer Identification: Application to Atracurium Besylate," Analytical Chemistry, vol. 71, No. 14, pp. 2838-2843 (1999).

Nehmer "Separation of cis-cis, cis-trans and trans-trans isomers of (.+−.)-atracurium besylate and cis and trans isomers of its major quaternary decomposition products and related impurity by reversed-phase high-performance liquid chromatography," Journal of Chromatography, vol. 457, pp. 127-135 (1988).

Stenlake et al: "Biodegradable Neuromuscular Blocking Agents 6. Stereochemical Studies on Atracurium and Related Polyalkylene Diesters," European Journal of Medicinal Chemistry, Editions Scientifique Elsevier, Paris, FR, vol. 19, No. 5, pp. 441-450 (Jan. 1, 1984).

Stenlake et al., "Neuromuscular Block Agents: Some approaches to short acting compounds," European Journal of Medicinal Chemistry, vol. 27, No. 5, pp. 463-477 (1992).

* cited by examiner

(1R,1'R)-ATRACURIUM SALTS SEPARATION PROCESS

TECHNICAL FIELD

The present invention relates to a method of separating the isomers of (1R,1'R)-atracurium salts by means of flash column chromatography.

BACKGROUND OF THE INVENTION

Cisatracurium besylate has the chemical name (1R,1'R,2R,2'R)-2,2'-[1,5-pentanediylbis[oxy(3-oxo-3,1-propanediyl)]]bis[1-[(3,4-dimethoxyphenyl)]methyl]-1,2,3,4-tetrahydro-6,7-dimethoxy-2-methyl-isoquinolinium dibenzenesulfonate and is represented by the structural formula (I) below:

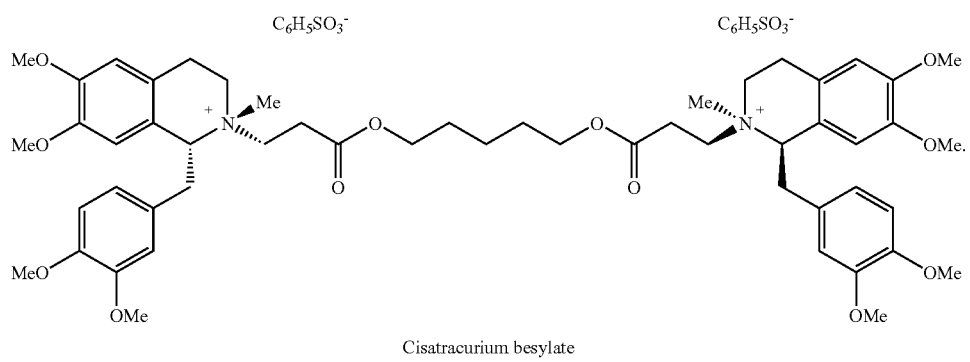

Cisatracurium besylate

Cisatracurium besylate is the dibenzenesulfonate salt of 1R-cis,1'R-cis isomer of atracurium (i.e., two molecules of benzenesulfonate per one diammonium molecule of cisatracurium). The atracurium molecule has four chiral centers, which should theoretically allow for 16 possible isomers. Due to the symmetry of the molecule, however, the number of possible isomers is reduced to 10. Cisatracurium besylate is one of the 10 possible isomers of atracurium besylate and may constitute approximately 15% of that mixture when produced by a conventional synthesis process.

Cisatracurium besylate is a nondepolarizing neuromuscular blocking agent indicated for inpatients and outpatients as an adjunct to general anesthesia, to facilitate tracheal intubation, and to provide skeletal muscle relaxation during surgery or mechanical ventilation in the Intensive Care Unit (ICU). Cisatracurium besylate possesses an activity that is superior to atracurium besylate, with significantly reduced side effects. Cisatracurium besylate is marketed in the United States and Europe by Glaxo Wellcome and Abbott Laboratories under the trade name NIMBEX®, which is a sterile, non-pyrogenic aqueous solution that is adjusted to pH 3.25 to 3.65 with benzenesulfonic acid. The drug is provided in 2.5 ml, 5 ml and 10 ml ampoules having a strength of 2 mg/ml cisatracurium besylate. A 30 ml vial containing 5 mg/ml cisatracurium besylate is also available.

Cisatracurium besylate slowly loses potency with time at a rate of approximately. 5% per year under refrigeration (5° C.). NIMBEX® should be refrigerated at 2° to 8° C. (36° to 46° F.) to preserve potency. The rate of loss in potency increases to approximately 5% per month at 25° C. (77° F.).

Atracurium besylate, otherwise known as 2,2'-[1,5-pentanediylbis[oxy(3-oxo-3,1-propanediyl)]]bis[1-[(3,4-dimethoxyphenyl)methyl]-1,2,3,4-tetrahydro-6,7-dimethoxy-2-methyl-isoquinolinium dibenzenesulfonate, is disclosed in U.S. Pat. No. 4,179,507 (hereinafter U.S. '507). U.S. '507 describes a series of bis veratryl isoquinolinium quaternary ammonium salts, preferably among them is atracurium besylate.

The synthesis of atracurium besylate, as taught in U.S. '507, involves the coupling of (±)-tetrahydropapaverine base, compound (II), with 1,5-pentamethylene diacrylate, compound (III). Treatment of the resulting tertiary amine base with oxalic acid results in the isolation of N,N'-4,10-dioxa-3,11-dioxotridecylene-1,13-bis-tetrahydro-papaverine dioxalate, compound (IV). The dioxalate salt (compound (IV) is converted to the free base, compound (V), with sodium bicarbonate solution and extracted into toluene. After evaporation of the toluene, the residue is dissolved in acetonitrile and treated with methyl benzenesulfonate. The addition of diethyl ether results in the precipitation of atracurium besylate, compound (VI), which is subsequently filtered and dried. Scheme 1 below illustrates the chemical pathway described above.

Scheme 1

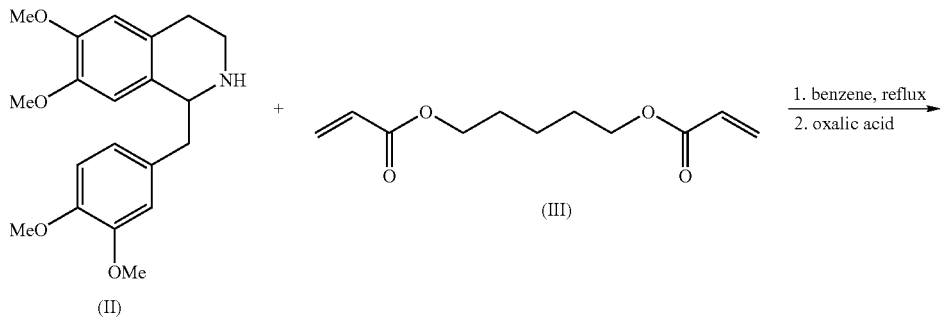

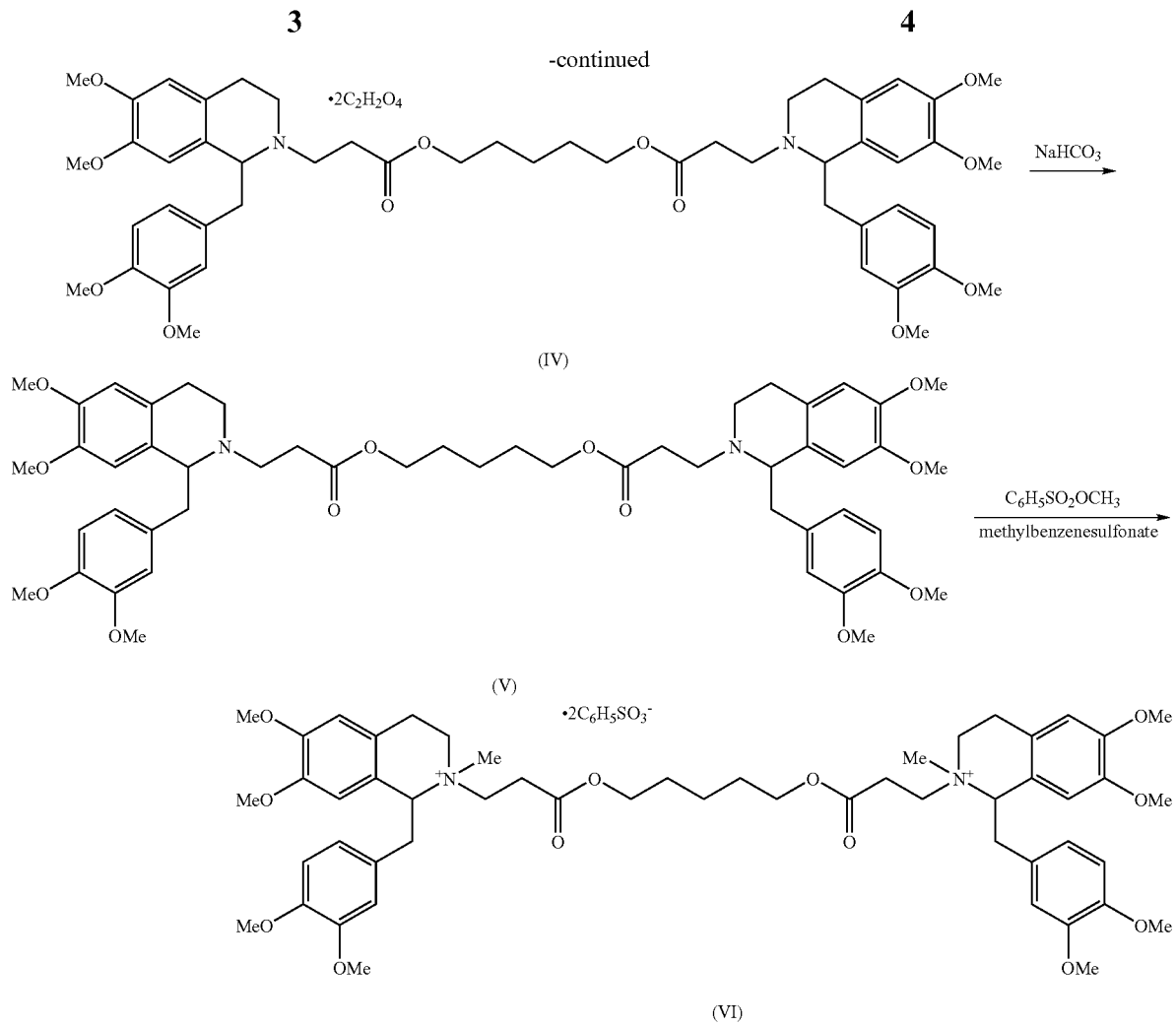

(IV)

(V)

(VI)

U.S. '507 teaches that the stereoisomerism of atracurium besylate (VI) may be partly controlled by controlling stereochemical configuration of compound (II) to provide the tertiary amine base (V) of a RR-, SS-, or RS-(meso) configuration. The quaternization process introduces 2 additional asymmetric centers and produces a mixture of stereoisomers. U.S. '507 does not describe separating stereoisomers from the mixture.

The preparation of cisatracurium besylate is disclosed in U.S. Pat. Nos. 5,453,510 and 5,556,978, wherein the (1R,1'R)-atracurium besylate mixture is subjected to preparative HPLC column chromatography on silica using a mixture of dichloromethane, methanol and benzenesulfonic acid in the ratio of 4000:500:0.25 as the eluant. The fractions containing the required isomer are collected and further processed to afford cisatracurium besylate possessing an isomeric purity of about 99%.

Conventional HPLC separation procedures suffer from the disadvantage that they require specialized equipment, which is relatively expensive and time-consuming to operate, and may not be suitable for large scale operations. There is, therefore, a need for an improved method for chromatographically purifying cisatracurium besylate, which is more suitable for large scale operations. The present invention provides such a method.

BRIEF SUMMARY OF THE INVENTION

The present invention provides an improved chromatographic process for obtaining the 1R-cis,1'R-cis isomer (cisatracurium besylate) from an isomer mixture containing the (1R-cis,1'R-cis); (1R-cis,1'R-trans) and (1R-trans,1'R-trans) isomers of (1R,1'R)-atracurium salts (e.g., the besylate salt), as well as other products. The process of the present invention is highly effective and more easily applicable for use on an industrial scale than conventional HPLC methods. The process of the present invention is versatile in that non-polar, polar protic and aprotic solvents can be used in the separation process. The process of the present invention can be performed using normal and reverse phase flash chromatography.

In one embodiment, the process of the present invention includes:

(a) loading a (1R,1'R)-atracurium salt (e.g., the besylate salt) isomer mixture onto a chromatographic column comprising a stationary phase suitable for flash chromatography;

(b) applying an eluant to elute from the column one or more fractions containing a cisatracurium salt, which is substantially free of other (1R,1'R)-atracurium isomers;

(c) collecting one or more of the fractions to obtain a cisatracurium salt, which is substantially free of other (1R,1'R)-atracurium isomers;

(d) optionally performing an ion exchange to convert the cisatracurium salt into cisatracurium besylate; and (e) isolating the cisatracurium besylate, e.g., in substantially purified form.

The process of the present invention can utilize stationary phases designed for normal phase or reverse phase flash chromatography. The stationary phase media utilized in normal phase flash chromatography typically is polar and contains silica or, e.g., one or more organic moieties containing amino and/or diol functional groups. The stationary phase media utilized in reverse phase flash chromatography typically is non-polar and includes silica which has been treated with octadecyl-($C_{18}$) ligands, although other ligands can be used such as octyl-($C_8$), butyl-($C_4$), tricosane-($C_{23}$) ligands, cyano or phenyl groups, as well as combinations thereof.

The mobile phase employed in the normal phase flash chromatography utilized in the process of the present invention preferably includes a non-polar or polar solvent such as hexane, toluene, diethyl ether, ethyl acetate, dichloromethane, chloroform, tetrahydrofuran (THF), methanol, ethanol, isopropanol, dimethylsulfoxide (DMSO), or a mixture thereof. The mobile phase employed in the reversed phase flash chromatography used in the process of the present invention preferably includes polar solvents as well as aprotic polar solvents such as, tetrahydrofuran, acetone, acetonitrile, N,N-dimethylformamide (DMF), dimethyl sulfoxide (DMSO), n-butanol, isopropanol, n-propanol, ethanol, methanol, dioxane, water or a mixture thereof.

The mobile phase employed in the reverse phase chromatographic process of the present invention preferably includes a pH-adjusting agent such as, for example, one or more organic and/or inorganic acids, one or more organic and/or inorganic bases, or a mixture thereof. The mobile phase employed in the reverse phase flash chromatographic process of the present invention preferably further includes a buffer substance that stabilizes the pH of the eluant. Suitable buffer substances can include, for example, phosphates, alkali metal or alkaline earth metal salts, such as sodium citrate or potassium acetate, ammonium citrate, and other salts containing, e.g., acetate, sulfate and/or chloride.

The average particle size of the stationary phase medium utilized in the process of the present invention preferably is from about 30 μm to about 200 μm, and more preferably is from about 35 μm to about 70 μm.

The process of the present invention preferably produces the desired 1R-cis,1'R-cis isomer (cisatracurium besylate) in an isomeric purity of at least about 97%, more preferably in an isomeric purity of at least about 99%, and most preferably in an isomeric purity of at least about 99.5%, as measured by HPLC.

DETAILED DESCRIPTION OF THE INVENTION

The present invention provides an improved chromatographic process for separating the isomers of (1R,1'R)-atracurium salts (e.g., the besylate salt) utilizing low to medium pressure (about 1-20 psi) flash chromatography which is rapid and more easily applicable on an industrial scale than conventional HPLC. The process of the present invention allows for the separation and purification of cisatracurium besylate from an isomeric mixture of (1R,1'R)-atracurium salt (e.g., the besylate salt).

The term "isomeric purity" as used herein, refers to the area percent of the peak corresponding to the 1R-cis,1'R-cis isomer relative to the total area percent of the (1R-cis,1'R-cis), (1R-cis,1'R-trans) and (1R-trans,1'R-trans) isomers.

The term "flash chromatography" as used herein, refers to a rapid preparative chromatographic method which utilizes an optimized stationary phase through which a liquid mobile phase (an eluant) is pumped at a high flow rate in order to separate the components (or analytes) of a mixture. These components typically are first loaded onto a flash chromatographic column and then forced to flow through a chromatographic column using the eluant and applying pressure. The pressure utilized in flash chromatography is in the low to medium range, and typically ranges from about 1 psi to about 20 psi, whereas conventional HPLC utilizes a pressure of from about 200 psi to about 5000 psi. The separation process of the present invention can utilize both normal and reverse phases.

The term "normal phase chromatography" refers to a mode of chromatography which typically utilizes a polar stationary phase containing silica or a stationary phase in which stable organic polar moieties containing cyano, amino and/or diol groups, among others, are attached to the silica surface. The average particle size of the stationary phase medium utilized in the normal phase flash chromatographic process of the present invention preferably is from about 30 μm to about 200 μm, and more preferably is from about 35 μm to about 70 μm whereas conventional HPLC utilizes a stationary phase with a particle size of from about 5 μm to about 10 μm. Thus, using optimized pre-packed column comprising a stationary phase with larger particle size, through which the solvent is pumped at relatively lower flow rate, enables simple and economical approach to preparative liquid chromatography.

The term "strong acids" refers to acids that dissociate practically completely (>99%) in aqueous solutions at standard temperature and pressure, such as benzenesulfonic acid, having a pKa value of 0 or lower, while the term "weak acids" refers to acids that partly dissociate in aqueous solutions, such as acetic acid, having a pKa value higher than 2.5.

The term "reverse phase chromatography" refers to a mode of chromatography which typically utilizes a non-polar stationary phase containing a silica surface, which is typically hydrophobically modified by treatment with one or more silylating agents such as, e.g., alkyl chlorosilanes, thus applying a covalently linked hydrophobic layer to the silica surface. The alkyl chains of such silanes are typically $C_{23}$, $C_{18}$, $C_8$ or $C_4$, cyano or phenyl, allowing for the retention of analytes while shielding the silica surface from attack and dissolution in aqueous mobile phases.

As used herein the term "substantially free of other isomers" means that no other isomers can be detected within the limits of the HPLC method.

The mobile phase utilized in the normal phase flash chromatographic process of the present invention preferably includes a non-polar or polar solvent such as hexane, toluene, diethyl ether, dichloromethane, chloroform, tetrahydrofuran (THF), ethyl acetate, isopropanol, ethanol, methanol, dimethyl sulfoxide (DMSO), or a mixture thereof.

The mobile phase utilized in the reverse phase flash chromatographic process of the present invention preferably includes polar solvents as well as polar aprotic solvents such as tetrahydrofuran (THF), acetone, acetonitrile, N,N-dimethylformamide (DMF), dimethyl sulfoxide (DMSO), n-butanol, n-propanol, methanol, ethanol, isopropanol, dioxane, water or a mixture thereof. The mobile phase employed in the reverse phase flash chromatographic process of the present invention preferably further includes a buffer substance that stabilizes the pH of the eluant system. Suitable buffer substances can include, for example, phosphates, alkali metal or alkaline earth metal salts and ammonium salts. Exemplary buffers include sodium citrate, potassium acetate, calcium or magnesium chloride or acetate, ammonium citrate, and other salts containing e.g., acetate, sulfate or chloride.

In one embodiment, the present invention provides a process for obtaining cisatracurium besylate, which includes the steps of:

(a) loading an (1R,1'R)-atracurium salt (e.g., the besylate salt) isomer mixture onto a chromatographic column comprising a stationary phase suitable for flash chromatography;

(b) applying an eluant to elute from the column one or more fractions containing a cisatracurium salt, which is substantially free of other (1R,1'R)-atracurium isomers;

(c) collecting one or more of the fractions, to obtain a cisatracurium salt, which is substantially free of other (1R, 1'R)-atracurium isomers;

(d) optionally performing an ion exchange to convert the cisatracurium salt into cisatracurium besylate so as to obtain cisatracurium besylate in substantially purified form; and (e) isolating the cisatracurium besylate.

The atracurium salt (e.g., the besylate salt) isomer mixture of step (a) may include a mixture of the (1R-cis,1'R-cis); (1R-cis,1'R-trans); and (1R-trans,1'R-trans)isomers, and also may contain one or more additional impurities, e.g., one or more synthesis by-products and/or impurities ordinarily associated therewith.

In accordance with the present invention, the (1R,1'R)-atracurium salt (e.g., the besylate salt) isomer mixture can be dissolved in an organic solvent, which can include a mixture of solvents, before being loaded onto the flash column. The solvent used for dissolving and loading the (1R,1'R)-atracurium salt (e.g., the besylate salt) isomer mixture onto the flash column preferably includes dichloromethane, methanol, DMSO or a mixture thereof.

The concentration (in molarity, M) of the (1R,1'R)-atracurium besylate isomer mixture in the solution that is applied to the chromatographic column is preferably in the range from about 0.1 M to about 0.5 M, and more preferably from about 0.1 M to about 0.3 M.

The flash chromatographic process of the present invention can include normal phase or reverse phase flash chromatography. The normal phase flash chromatographic process of the present invention preferably utilizes a flash column with a stationary phase that contains silica or, e.g., one or more organic moieties containing cyano, amino and/or diol functional groups. The reverse phase flash chromatographic process of the present invention preferably utilizes a flash column with a stationary phase that includes silica which has been hydrophobically modified with one or more organic residues containing linear hydrocarbon chains suitable for reverse phase flash chromatography. Preferably, the linear hydrocarbon chain is a $C_{18}$, $C_8$, $C_4$ or $C_{23}$ hydrocarbon chain. The reverse phase flash chromatographic column utilized in accordance with the present invention also can contain a stationary phase containing silica which has been hydrophobically modified with one or more organic residues containing cyano or phenyl groups suitable for reverse phase flash chromatography.

In accordance with the present invention, the eluant used in step (b) preferably is a non-aqueous mobile phase containing an organic acid. The mobile phase utilized in the normal phase flash chromatographic process of the present invention includes a non-polar or polar solvent such as hexane, toluene, diethyl ether, dichloromethane, chloroform, tetrahydrofuran (THF), ethyl acetate, isopropanol, ethanol, methanol, dimethyl sulfoxide (DMSO), or a mixture thereof. Preferably, the organic solvent includes dichloromethane, methanol, DMSO, or a mixture thereof.

Suitable organic acids, which can be used in the eluant used in step (b), can include a weak or strong organic acid. Suitable weak organic acids include, e.g., formic acid, acetic acid and propionic acid. A preferred weak organic acid is acetic acid. Suitable strong organic acids include, e.g., benzenesulfonic acid, methanesulfonic acid, and p-toluenesulfonic acid. A preferred strong organic acid is benzenesulfonic acid.

In one embodiment of the present invention, the flash column is eluted with a mobile phase containing dichloromethane, DMSO and acetic acid. Preferably, the dichloromethane:DMSO:acetic acid ratio in the eluant mixture is about 70-85 (volumes dichloromethane), 8-20 (volumes DMSO) and 5-15 (volumes acetic acid). In another embodiment of the present invention, the flash column is eluted with a mobile phase containing dichloromethane, methanol and benzenesulfonic acid. Preferably, the dichloromethane:methanol:benzenesulfonic acid ratio in the eluant mixture is about 93 (volumes dichloromethane), 7 (volumes methanol) and 0.006 (weight benzenesulfonic acid).

In accordance with the present invention, an ion exchange step can be performed, e.g., to afford the desired besylate anion or otherwise to convert other cisatracurium salts that may exist in the eluant into the besylate salt. The ion exchange step preferably is performed by contacting the eluted material with an ion exchange resin carrying benzenesulfonate anions. The ion exchange process can be performed, e.g., by acidifying one or more collected fractions after the separation process with an aqueous benzenesulfonic acid solution to a pH of about 3, and applying the solution to an ion exchange column. The cisatracurium besylate can be removed from the column, e.g., by eluting the column with an organic solvent such as, e.g., methanol, ethanol, isopropanol, acetone, methyl ethyl ketone, acetonitrile or a mixture thereof. A preferred solvent for eluting cisatracurium besylate from an ion exchange column is methanol.

The isolation step (e) preferably includes:

(i) optionally evaporating at least a portion of an organic solvent;

(ii) adding water and adjusting the pH of the mixture to about 3 with an aqueous benzenesulfonic acid solution; and (iii) drying the aqueous phase to obtain the product.

Preferably, the drying is performed by spray drying or freeze drying.

The process of the present invention preferably produces cisatracurium besylate in an isomeric purity of at least about 97%, more preferably in an isomeric purity of at least about 99%, and most preferably in an isomeric purity of at least about 99.5%, as measured by HPLC. The process of the present invention preferably also produces cisatracurium besylate containing less than about 0.5% of other isomers, as measured by HPLC.

The following examples further illustrate the invention but, of course, should not be construed as in any way limiting its scope.

In the following examples 1 and 2, flash chromatographic separations were performed on an (1R,1'R)-atracurium besylate isomer mixture using a variety of eluant systems employing silica as the stationary phase.

Method description: A (1R,1'R)-atracurium besylate isomer mixture consisting of about 58% (1R-cis,1'R-cis); 36% (1R-cis,1'R-trans) and 6% (1R-trans,1'R-trans) was separated by flash chromatography.

In the following example 3, flash chromatographic separations were performed on an (1R,1'R)-atracurium besylate isomer mixture using a variety of eluant systems employing reverse phase as the stationary phase.

Analytical reference solution: An analytical reference solution (2.07 mM) of (1R,1'R)-atracurium besylate isomer mixture, was prepared and kept cold for use in the identification and quantitative analysis of the isomers.

Example 1

This example demonstrates a normal-phase flash separation.

The normal-phase column that has been used was RediSep®, Disposable Flash Column, produced by Teledyne Isco, Inc., Lincoln, Nebr., USA, Cat.no. 68-2203-027, 17×3 cm (40 gram), average particle size 35-70 microns, average pore size 60A. Eluant: dichloromethane:DMSO:acetic acid 76:14:10 (v/v), detection: 280 nm, flow rate: 20 ml/min. 304.7 mg of (1R,1'R)-atracurium besylate isomer mixture consisting of 55.5% 1R-cis,1'R-cis; 35% 1R-cis,1'R-trans and 5.6% 1R-trans,1'R-trans was dissolved in 3 ml of the eluant and loaded into the column. The injected volume was 50 ml. The elution of cisatracurium began after 280 ml of eluant was passed through the column. Fractions of column eluate (the total fraction volume was 20-30 ml), containing 1R-cis-1R'-cis isomer, were collected and analyzed against the analytical reference solution. Table 1 details, inter alia, the sample concentration, and the calculated weight of the 1R-cis,1'R-cis isomer, which was eluted into the column.

Table 4 summarizes, inter alia, the amount of the cisatracurium as besylate estimated by HPLC and the yield of the cisatracurium besylate.

TABLE 4

Total loading of the cisatracurium besylate-165 mg

| No. | Isomeric purity (%) | Total purity (%) | Amount of the cisatracurium as besylate (mg)-estimated by HPLC | Yield of the cisatracurium besylate (%) |
|---|---|---|---|---|
| 1 | >99.5 | >98 | 48.6 | 29.5 |
| 2 | >99.9 | >94 | 42.6 | 25.8 |
| 3 | 100 | >80 | 19.6 | 11.9 |
| Total | | | 110.8 | 67.2 |

Yield of >99.5% isomeric purity product = 67.2%
Yield of >98% total purity product = 29.5%

TABLE 1

| Sample concentration (mg/ml) | Injected volume, μl | % of the cis-cis isomer in the mixture | calculated weight of the cis-cis isomer entered the column (mg/column) | Concentration of the atracurium isomers cation (mg/ml) | Concentration of the cisatracurium cation (mg/ml) | calculated weight of the cis-cis cation entered the column (mg/column) |
|---|---|---|---|---|---|---|
| 2.13 | 10 | 55.4 | 0.01 | 1.59 | 0.9 | 0.09 |

Table 2 details, inter alia, the isomeric fraction purity, total fraction purity, and total content of the cisatracurium cation.

TABLE 2

| Fraction No. | Total fraction volume, ml | Total content of the cisatracurium cation, mg | Expected amount of cisatracurium besylate, mg | Cis-trans isomer content, % * | Total fraction purity, % ** | Isomeric fraction purity, % *** |
|---|---|---|---|---|---|---|
| 1 | 30 | 0.2 | 0.3 | 0.0 | 36.0 | 100.0 |
| 2 | 30 | 1.6 | 2.1 | 0.0 | 59.0 | 100.0 |
| 3 | 30 | 6.6 | 8.9 | 0.0 | 82.7 | 100.0 |
| 4 | 20 | 8.0 | 10.7 | 0.0 | 91.6 | 100.0 |
| 5 | 20 | 9.5 | 12.7 | 0.0 | 95.3 | 100.0 |
| 6 | 20 | 9.6 | 12.9 | 0.0 | 97.0 | 100.0 |
| 7 | 20 | 9.0 | 12.1 | 0.1 | 97.5 | 99.9 |
| 8 | 20 | 8.0 | 10.8 | 0.1 | 98.4 | 99.9 |
| 9 | 20 | 7.0 | 9.3 | 0.1 | 98.4 | 99.9 |
| 10 | 30 | 8.6 | 11.6 | 0.1 | 98.4 | 99.9 |
| 11 | 20 | 4.7 | 6.4 | 0.1 | 98.4 | 99.9 |
| 12 | 20 | 4.0 | 5.3 | 0.1 | 96.5 | 99.9 |
| 13 | 20 | 3.1 | 4.1 | 0.1 | 99.3 | 99.9 |
| 14 | 20 | 2.6 | 3.5 | 0.2 | 98.9 | 99.7 |
| 15 | 20 | 2.3 | 3.0 | 0.5 | 98.3 | 99.5 |
| 16 | 20 | 1.9 | 2.5 | 1.1 | 97.7 | 98.9 |
| 17 | 20 | 1.7 | 2.2 | 2.1 | 96.4 | 97.9 |
| 18 | 20 | 1.4 | 1.9 | 3.9 | 94.1 | 96.0 |

Note:
The trans-trans isomer was not present in the collected fractions
* Cis-trans isomer content (%) = [area of cis-trans isomer/sum of all areas] × 100
** Total fraction purity (%) = [area of cis-cis isomer/sum of all areas] × 100
*** Isomeric purity (%) = [area of cis-cis isomer/(area of cis-cis isomer + area of cis-trans isomer + area of trans-trans isomer)] × 100.

Table 3 summarizes the results for the combined fractions.

TABLE 3

| Loading volume (ml) | Loading concentration (M) | % Cis-cis isomer in the (1R,1'R)-atracurium mixture | % Isomer purity of the cis-cis isomer | Amount of the cis-cis isomer (mg) | Yield of the cis-cis isomer (%) |
|---|---|---|---|---|---|
| 5 | 0.290 | 58 | 99.4 | 599.6 | 60 |

Example 2

This example demonstrates a normal-phase flash separation.

This column that has been used was RediSep® (see Example 1). Eluant:dichloromethane:methanol:benzenesulfonic acid in a ratio of 93:7:0.006 (v/v/w), detection: 280 nm, flow rate: 25 ml/min. The sample solution for flash chromatography separation was prepared by dissolving 1.45 g of the (1R,1'R)-atracurium besylate isomer mixture in 3 ml of dichloromethane mixture. The solution was loaded onto the column. The cisatracurium began to elute after about 675 ml of eluant mixture was passed through the column. Fractions of the column eluate were collected and analyzed against the analytical reference solution. Those fractions containing the required 1R-cis,1'R-cis isomer were combined. Table 5 summarizes the results for the combined fractions.

TABLE 5

| Fraction | Loading volume (ml) | Loading concentration (M) | % of the cis-cis isomer in the (1R,1'R)-atracurium mixture | % Isomer purity of the cis-cis isomer | Amount of the cis-cis isomer (mg) | Yield of the cis-cis isomer (%) |
|---|---|---|---|---|---|---|
| Combined | 3 | 0.389 | 58 | 99.9 | 513.9 | 59 |

Example 3

This example demonstrates a reversed-phase flash separation.

The reversed-phase HPLC column that has been used was RediSep®, Reversed phase C18, produced by Teledyne Isco, Inc., Lincoln, Nebr., USA, Cat.no.68-2203-030, 43 g, average particle size 40-63 microns. The R,R'-atracurium besylate mixture was eluted on the C18 stationary phase using the following eluants:

Eluant A: 20mM NaNO$_3$ aqueous solution (pH=2.0 with HNO$_3$), Eluant B: MeOH Flash System: CombiFlash, produced by Teledyne Isco, Inc.

Flow rate: 20 ml/min

Mobile phase composition:

| Time (minutes) | % Eluant A | % Eluant B |
|---|---|---|
| 0-10 | 70 | 30 |
| 10-17 | 65 | 35 |
| 17-onwards | 60 | 40 |

100 mg of (1R, 1'R) atracurium besylate isomer mixture, consisting of 53.6% 1R-cis,1'R-cis; 30.8% 1R-cis,1'R-trans and 4.8% 1R-trans,1'R-trans, was dissolved in 2 ml of the initial eluant composition (70% Eluant A and 30% Eluant B) and loaded into the column. The elution of the fractions containing more than 65% cisatracurium isomer began after passing 1000 ml of eluant through the column. Fractions of the column eluate containing the 1R-cis-1'R-cis isomer were collected and analyzed against the analytical reference solution, as detailed in Table 6.

TABLE 6

| Fraction no. | Total content of the cisatracurium cation, mg | Expected amount of the cisatracurium besylate, mg | Cis-trans isomer content (%)* | Trans-trans isomer content (%)* | Fraction purity (%)** | Isomeric fraction purity (%)*** |
|---|---|---|---|---|---|---|
| 1 | 2.4 | 3.2 | 31.7 | 0.5 | 67.5 | 67.7 |
| 2 | 2.4 | 3.2 | 26.5 | 0.2 | 73.1 | 73.2 |
| 3 | 2.4 | 3.2 | 21.7 | 0.2 | 78.0 | 78.1 |
| 4 | 2.3 | 3.1 | 17.2 | 0.1 | 82.5 | 82.7 |
| 5 | 2.2 | 3.0 | 13.7 | 0.1 | 86.3 | 86.3 |
| 6 | 2.0 | 2.7 | 10.4 | 0.1 | 89.3 | 89.5 |
| 7 | 2.0 | 2.7 | 7.8 | 0.1 | 91.5 | 92.0 |
| 8 | 1.6 | 2.2 | 5.8 | 0.1 | 92.9 | 93.4 |
| 9 | 1.7 | 2.2 | 5.7 | 0.1 | 93.9 | 94.2 |
| 10 | 1.5 | 2.0 | 5.0 | 0.0 | 94.9 | 95.0 |
| 11 | 1.4 | 1.9 | 4.5 | 0.0 | 95.4 | 95.5 |
| 12 | 1.3 | 1.7 | 4.1 | 0.0 | 95.7 | 95.9 |
| 13 | 1.2 | 1.5 | 3.9 | 0.0 | 95.8 | 96.1 |
| 14 | 1.1 | 1.4 | 3.7 | 0.0 | 96.3 | 96.3 |
| 15 | 0.9 | 1.2 | 3.4 | 0.0 | 96.3 | 96.6 |
| 16 | 0.8 | 1.1 | 3.2 | 0.0 | 96.6 | 96.8 |
| 17 | 0.8 | 1.0 | 3.0 | 0.0 | 96.7 | 97.0 |
| 18 | 0.7 | 0.9 | 2.8 | 0.0 | 96.9 | 97.2 |
| 19 | 0.7 | 0.9 | 2.8 | 0.0 | 97.2 | 97.2 |
| 20 | 0.6 | 0.8 | 2.7 | 0.0 | 96.4 | 97.3 |
| 21 | 0.5 | 0.7 | 2.5 | 0.0 | 96.7 | 97.5 |
| 22 | 0.5 | 0.6 | 2.4 | 0.0 | 96.6 | 97.6 |
| 23 | 0.4 | 0.5 | 2.6 | 0.0 | 95.4 | 97.4 |

TABLE 6-continued

| Fraction no. | Total content of the cisatracurium cation, mg | Expected amount of the cisatracurium besylate, mg | Cis-trans isomer content (%)* | Trans-trans isomer content (%)* | Fraction purity (%)** | Isomeric fraction purity (%)*** |
|---|---|---|---|---|---|---|
| 24 | 0.3 | 0.4 | 2.3 | 0.0 | 94.5 | 97.6 |
| 25 | 0.4 | 0.5 | 2.6 | 0.0 | 95.4 | 97.4 |

Note:
the trans-trans isomer is not present in the collected fractions
*Cis-trans isomer content (%) = [area of the cis-trans isomer/sum of all areas] × 100
**Total fraction purity (%) = [area of the cis-cis isomer/sum of all areas] × 100
***Isomeric purity (%) = [area of the cis-cis isomer/(area of the cis-cis isomer + area of the cis-trans isomer + area of trans-trans isomer)] × 100

The results are presented in Table 7.

TABLE 7

| No. | Isomeric purity, % | Total purity, % | Amount of the cisatracurium besylate estimated by HPLC, mg | Yield of the cisatracurium besylate, % |
|---|---|---|---|---|
| Total loading of the cisatracurium besylate-53.6 mg | | | | |
| 1 | >95 | >95 | 21.7 | 40.5 |
| 2 | >97 | >95 | 6.3 | 11.8 |

Example 4

This example demonstrates a method of performing a work-up procedure to isolate cisatracurium besylate after the flash chromatography.

The collected fractions after the column separation, containing the cisatracurium besylate, were washed four times with 10% brine that was acidified to pH 2 with an aqueous benzenesulfonic acid solution and then applied to a pretreated strong anion exchange column or cartridge (SAX). (The pretreatment consisted of passing 600 ml of 0.1M aqueous benzenesulfonic acid solution through the cartridge in order to substitute chloride anions with benzenesulfonate anions. Subsequently, the cartridge was conditioned by passing 300 ml methanol followed by 300 ml dichloromethane through the cartridge). The cisatracurium cation was retained by the cartridge. The cisatracurium besylate was eluted from the cartridge with methanol. The methanol solution was dried over magnesium sulfate and evaporated. The residual oil was dissolved in water. The pH was adjusted to about 3 with a benzenesulfonic acid solution. The aqueous solution was lyophilized to afford a solid containing only cisatracurium besylate as identified by HPLC and NMR. The yield of recovered cisatracurium besylate from the atracurium besylate isomer mixture was about 60%.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of separating the 1R-cis,1'R-cis isomer (cisatarcurium) from (1R,1'R)-atracurium salt isomer mixture, the method comprising:
   (a) loading the (1R,1'R)-atracurium salt isomer mixture onto a chromatographic column comprising a stationary phase suitable for normal phase flash chromatography;
   (b) eluting with an eluant at low to medium pressure, to elute from the column one or more fractions comprising a cisatracurium salt, which is substantially free of other (1R,1'R)-atracurium isomers;
   (c) collecting one or more of the fractions, to obtain a cisatracurium salt, which is substantially free of other (1R,1'R)-atracurium isomers;
   (d) optionally performing an ion exchange; and
   (e) isolating the cisatracurium salt
   wherein step (b) comprises eluting with a non-aqueous mobile phase comprising a weak organic acid.

2. The method of claim 1, wherein the non-aqueous mobile phase comprises hexane, toluene, diethyl ether, ethyl acetate, dichloromethane, chloroform, tetrahydrofuran (THF), methanol, ethanol, isopropanol, dimethylsulfoxide (DMSO), or a mixture thereof.

3. The method of claim 2, wherein the non-aqueous mobile phase comprises dichloromethane, methanol, dimethyl sulfoxide (DMSO) or a mixture thereof.

4. The method of claim 1, wherein the weak organic acid is formic acid, acetic acid or propionic acid.

5. The method of claim 4, wherein the weak organic acid is acetic acid.

6. The method of claim 1, wherein the eluant comprises dichloromethane, DMSO and acetic acid in a ratio ranging from 70-85 (volumes dichloromethane): 5-20 (volumes DMSO):5-15 (volumes acetic acid).

7. The method of claim 1, comprising performing step (d), wherein step (d) comprises contacting an eluted material with an ion exchange resin carrying benzenesulfonate anions.

8. The method of claim 1, wherein step (e) comprises adjusting the pH of an aqueous cisatracurium besylate solution to 3 with an aqueous benzenesulfonic acid solution.

9. The method of claim 1, wherein step (e) comprises freeze drying or spray drying.

10. The method of claim 1, wherein the cisatracurium salt obtained in step (e) is cisatracurium besylate having an isomeric purity of at least 97%.

11. The method of claim 10, wherein the cisatracurium salt obtained in step (e) is cisatracurium besylate having an isomeric purity of at least 99%.

12. The method of claim 11, wherein the cisatracurium salt obtained in step (e) is cisatracurium besylate having an isomeric purity of at least 99.5%

* * * * *